(12) United States Patent
Braun et al.

(10) Patent No.: US 10,775,337 B2
(45) Date of Patent: Sep. 15, 2020

(54) POTENTIAL GRADIENT AMPLIFIED DETECTION OF CHEMICAL AGENTS

(71) Applicant: The Board of Trustees of the University of Illinois, Urbana, IL (US)

(72) Inventors: Paul V. Braun, Champaign, IL (US); Mohammad Amdad Ali, Urbana, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 314 days.

(21) Appl. No.: 15/880,815

(22) Filed: Jan. 26, 2018

(65) Prior Publication Data

US 2018/0217085 A1 Aug. 2, 2018

Related U.S. Application Data

(60) Provisional application No. 62/451,389, filed on Jan. 27, 2017.

(51) Int. Cl.
| | |
|---|---|
| *G01N 1/40* | (2006.01) |
| *G01N 27/403* | (2006.01) |
| *G01N 27/333* | (2006.01) |
| *C12Q 1/44* | (2006.01) |
| *G01N 33/00* | (2006.01) |
| *C08L 33/26* | (2006.01) |

(Continued)

(52) U.S. Cl.
CPC ............ *G01N 27/333* (2013.01); *C08L 33/26* (2013.01); *C12Q 1/005* (2013.01); *C12Q 1/44* (2013.01); *C12Y 301/08002* (2013.01); *G01N 1/40* (2013.01); *G01N 1/405* (2013.01); *G01N 1/4044* (2013.01); *G01N 27/403* (2013.01); *G01N 27/44747* (2013.01); *G01N 33/0013* (2013.01); *G01N 33/0057* (2013.01); *C08L 2201/54* (2013.01); *G01N 33/559* (2013.01); *G01N 2333/916* (2013.01); *Y02A 50/25* (2018.01)

(58) Field of Classification Search
CPC ...... G01N 27/44747; G01N 1/28; G01N 1/40; G01N 33/558; G01N 33/559; G01N 27/333; G01N 27/403
See application file for complete search history.

(56) References Cited

PUBLICATIONS

Hadjout et al., "Automated Real-Time Measurements of Leukocyte Chemotaxis," J Immunol Methods Mar. 30, 2007; 320(1-2); 70-80 (Year: 2007).*

(Continued)

*Primary Examiner* — Alexander S Noguerola
(74) *Attorney, Agent, or Firm* — Haukaas Fortius PLLC; Michael H. Haukaas (57) ABSTRACT

New approaches for selective detection of chemical agents such as sarin are necessary because of the high toxicity of sarin and related compounds, the potential of these compounds to be used as weapons of mass destruction, and the limitations of current detection methodologies. Herein is described an apparatus and a method for selective and amplified detection of sarin simulants deposited via an aerosol process. The simulant absorbs into a hydrogel, where it hydrolyzes upon contact with water producing elemental ions. The elemental ions are then concentrated via an ionic chemical potential gradient to a sensor, where it is detected. This technique has potential to amplify the capture efficiency of a sensor by a 1000-fold within couple of minutes.

20 Claims, 6 Drawing Sheets

(51) Int. Cl.
     *C12Q 1/00*           (2006.01)
     *G01N 27/447*      (2006.01)
     *G01N 33/559*      (2006.01)

(56) References Cited

PUBLICATIONS

Sitt et al., "Directed Transport by Surface Chemical Potential Gradients for Enhancing Analyte Collection in Nanoscale Sensors," Nano Lett., 15(5):3341-3350, May 2015.
Zhang et al., "Autonomic Molecular Transport by Polymer Films Containing Programmed Chemical Potential Gradients," (Supporting Information) J Am Chem Soc., 137(15):5066-5073, Apr. 2015.
Zhang et al., "Autonomic Molecular Transport by Polymer Films Containing Programmed Chemical Potential Gradients," J Am Chem Soc., 137(15):5066-5073, Apr. 2015.

* cited by examiner

ABSTRACT

POTENTIAL GRADIENT AMPLIFIED DETECTION OF CHEMICAL AGENTS

RELATED APPLICATIONS

This application claims priority under 35 U.S.C. § 119(e) to U.S. Provisional Patent Application No. 62/451,389, filed Jan. 27, 2017, which is incorporated herein by reference.

GOVERNMENT SUPPORT

This invention was made with government support under Grant No. HDTRA1-12-1-0035 awarded by the Department of Defense. The government has certain rights in the invention.

BACKGROUND OF THE INVENTION

The highly toxic G-type nerve agents, which include sarin (GB), soman (GD), and cyclosarin (GF) are considered weapons of mass destruction. Upon inhalation or dermal penetration, they attack the nervous system by interfering the degradation of neurotransmitter acetylcholine leading to death. Permanent damage to the nervous system can also occur at non-lethal doses. Immediate application of antidotes to an affected person could prevent permanent damage. However, exposure to low levels of nerve agent leads to ambiguous signs and symptoms that cannot be easily discriminated from other conditions. The inability to detect nerve agents at low-concentration may result in a delay in treatment and permanent damage.

Extensive efforts have been made to develop sensors for sarin and similar compounds, however, detection below ppb level remains a difficulty. To overcome this limitation, pre-concentration techniques are frequently used to detect target molecules from the air. However, pre-concentration techniques have their own challenges, particularly in the field, including that they can be time consuming.

Chemical gradients in hydrogel films have been reported to concentrate model analytes, such as charged dye molecules, at least 40-fold by biasing diffusion such that the dye is directionally transported to a central point in the film at a rate of few micromeres per minute. While the concept of gradient-directed transport is attractive because it enhances the sensor response, the slow transport velocity limits the applicability for real time detection. This also assumes an appropriate read-out mechanism exists for the concentrated analyte.

Existing techniques to not adequately address the need for a simple field solution to detect trace levels of chemical agents. Accordingly, a better solution for the selective and rapid detection of chemical agents at very low concentrations is needed.

SUMMARY

Figure 6:
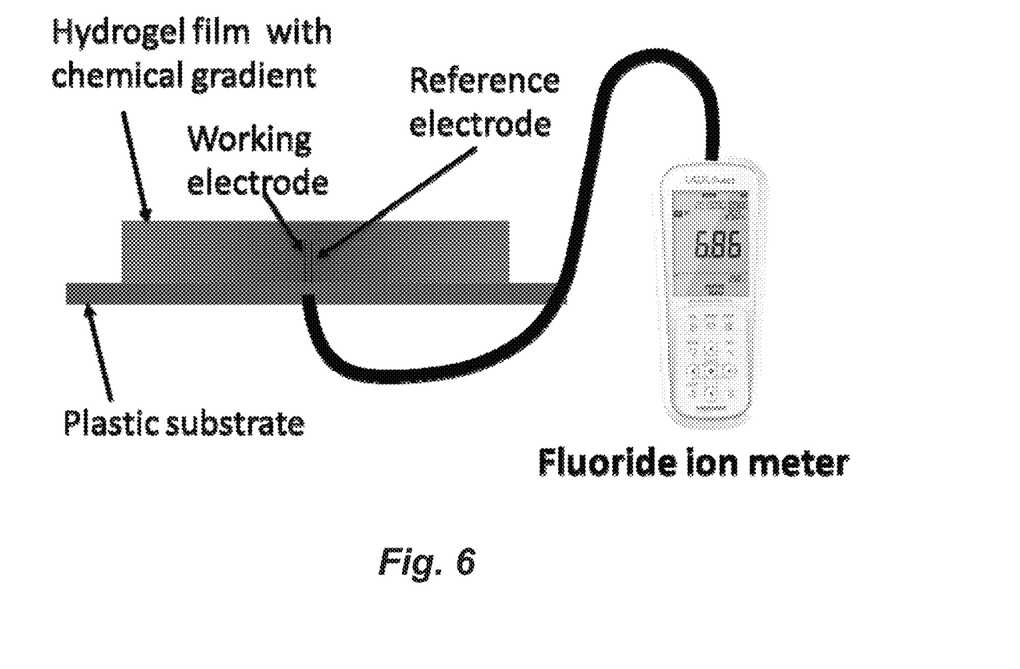
FIG. 6. Prototype device of one embodiment for detection of sarin.

Demonstrated herein is the gradient-directed transport of $Cl^-$, $F^-$, and protons within hydrogel films containing embedded chemical gradients. The rational for studying the directional transport of protons, $Cl^-$, and $F^-$ through a hydrogel is several-fold. First, a typical hydrogel contains considerable water and the P—F bond in sarin is rapidly hydrolyzed in presence of water yielding $F^-$, and many nerve agent simulants such as diethyl chlorophosphate, hydrolyze yielding $Cl^-$). Second, monovalent elemental ions diffuse considerably faster than molecules on the size of sarin. Finally, there are well-established electrochemical and fluorescent dye-based protocols for detecting $Cl^-$ and $F^-$ (FIG. 6).

Accordingly, this disclosure provides a polymer gel for detection of elemental ions comprising:

a) a polymer gel having a chemical potential gradient that can concentrate elemental ions by enthalpy driven transport; and b) a plurality functional of groups, wherein the polymer gel is covalently bonded to the functional groups that provide the chemical potential gradient that transports the elemental ions to a region where the elemental ions are concentrated;

wherein an analyte in contact with the polymer gel is dissociated into molecular ions and elemental ions, and the elemental ions are transported by the chemical potential gradient of functional groups to the region where the elemental ions are concentrated.

This disclosure also provides an autonomic ion detector comprising:

a) a polymer gel having at least one chemical potential gradient that can concentrate elemental ions by enthalpy driven transport, wherein the elemental ions are halide ions, hydrogen ions, or a combination thereof;

b) a catalyst dispersed in the polymer gel to catalyze the dissociation of a sample into elemental ions and molecular ions;

c) a plurality functional groups comprising a quaternary amine moiety, a sulfate moiety, a nitrate moiety, a tertiary amine moiety, a borate moiety, or a combination thereof;

wherein the polymer gel is covalently bonded to the functional groups that provide the chemical potential gradient that transports the elemental ions to a region where the ions are concentrated; and d) an electrode to detect elemental ions at the region where the elemental ions are concentrated;

wherein a sample in contact with the autonomic ion detector is dissociated into molecular ions and elemental ions, and the elemental ions are transported by the chemical potential gradient of functional groups to the region where the elemental ions are concentrated and detected.

Additionally, this disclosure provides a method of detecting elemental ions comprising:

a) contacting a sample with a polymer gel having at least one chemical potential gradient that can concentrate elemental ions by enthalpy driven transport;

wherein the polymer gel is covalently bonded to a plurality of functional groups that provide the chemical potential gradient that transports the elemental ions to a region where the elemental ions are concentrated; and b) detecting the concentration of elemental ions with an electrode at the region where the elemental ions are concentrated;

wherein the sample comprises one analyte, or two or more different analytes that are dissociated by contacting the polymer gel into molecular ions and elemental ions, and the elemental ions are transported by the chemical potential gradient of functional groups to the region where the elemental ions are concentrated and detected.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1. (a) Synthesis of cationic quaternary ammonium functionalized polyacrylamide (PAAm) hydrogel used as the basis for the $Cl^-$ transporting gradient assuming high conversion yield for the functionalization step. (b,c) Schematics of setups for localized hydrolysis used for creating directional and radially symmetric chemical gradients in the PAAm films. (d) Illustration of the enthalpy profile for the $Cl^-$ in gradient-containing PAAm films: (i) directional gradient, (ii) radially symmetric gradient. Blue spheres represent $Cl^-$. The enthalpy landscape is due to electrostatic interactions between the cationic gradient and $Cl^-$.

FIG. 2. (a) Schematic, and (b) fluorescence images at increasing times of diffusion of Cl– in a gradient-free hydrogel, (c) Schematic, and (d) fluorescence images at increasing times of the directional transport of $Cl^-$ by a cationic quaternary ammonium gradient. (e) Schematic, and (f) optical images at increasing times of the directional transport of $H^+$ by an anionic sulfate gradient.

FIG. 3. (a) Schematic of aerosol-dosed $Cl^-$ concentration by a neutral-to-cationic radially symmetric gradient. Yellow spheres represent $Cl^-$. The ion diffuses randomly outside of the gradient and directionally within the gradient. The back line illustrates the trajectory of specific $Cl^-$. (b) Fluorescence images of the surface at increasing times. (c) Line profiles of fluorescence intensity intersecting the origin of radially symmetric gradient indicated by the dashed lines in (b).

FIG. 4. (a) Hydrolysis of sarin simulant, diethyl chlorophosphate, in the presence of water in the PAAm hydrogel. (b) Fluorescence image of a PAAm hydrogel containing both gradient and gradient-free regions, 30 min after diethyl chlorophosphate dosing. The line profile of fluorescence intensity intersecting the origin of radially symmetric gradient shown on the left is indicated by the dashed line.

FIG. 7. (a) Hydrolysis of aerosol-dosed sarin simulant, diisopropyl fluorophosphate, in presence of enzyme, diisopropyl fluorophosphatase. (b) Schematic diagram of an experimental setup to monitor fluoride ion activities using electrochemical sensor. Enzymes were immobilized within a thin layer of PAAm gels (~5 μm) and a PAAm (~100 μm) gel contains a neutral-to-cationic radially symmetric gradient to concentrate fluoride ion. (c) Plot of fluoride ion in gels (assuming all absorbed simulants were hydrolyzed) versus concentration of fluoride ion measured by fluoride ion sensor at center and outside of the gradient.

DETAILED DESCRIPTION

Figure 5:
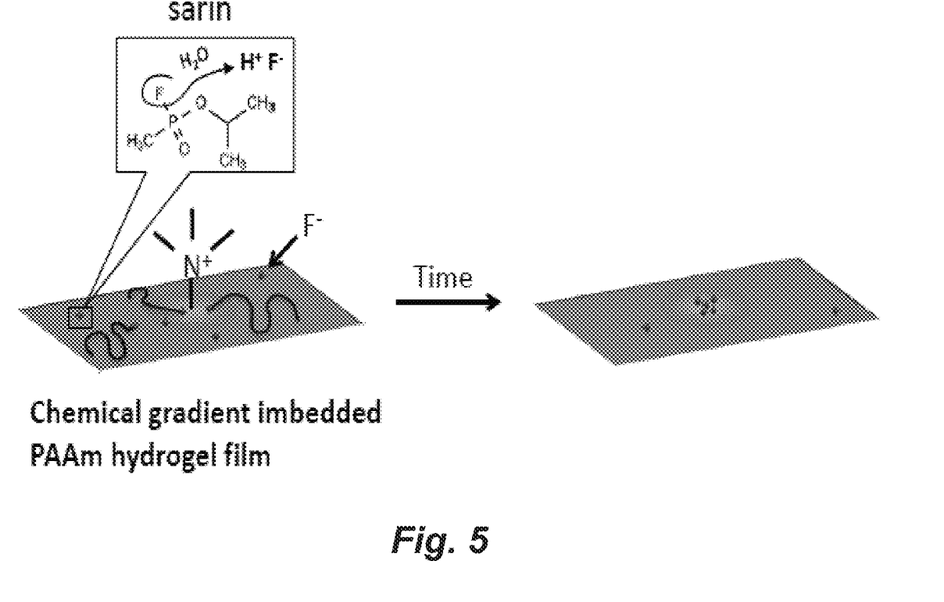
FIG. 5. A strategy for sarin detection of one embodiment. Sarin is hydrolyzed within minutes upon contact with a nucleophilic agent dispersed in hydrogel, producing $F^-$ ions. Radially symmetric chemical gradient drives $F^-$ ions towards sensor. 1000-fold enhancement of detection limit could be achieved within couple of minutes.

The disclosed polyacrylamide (PAAm)-based hydrogels were chosen as a transport media because they can be easily functionalized and are relatively robust to a variety of chemical environments. It was demonstrated that a cationic quaternary ammonium-based gradient could directionally transport anions such as $Cl^-$ and $F^-$, and a sulfate-based anionic gradient could directional transport cations such as $H^+$. As the proof of the concept for enhancing the detectability of a chemical warfare agent, diethyl chlorophosphate was used as a substitute of sarin for safety. Diethyl chlorophosphate was sprayed on the radially symmetric quaternary ammonium ionic gradient built-in hydrogel film and the hydrolyzed product, $Cl^-$ was concentrated at a defined location as a function of time (FIG. 5).

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%. For example, repeat unit A is substantially soluble (e.g., greater than about 95% or greater than about 99%) in a polar organic solvent and is substantially insoluble (e.g., less than about 5% or less than about 1%) in a fluorocarbon solvent. In another example, repeat unit B is substantially soluble (e.g., greater than about 95% or greater than about 99%) in a fluorocarbon solvent and is substantially insoluble (e.g., less than about 5% or less than about 1%) in a polar organic solvent.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, ... 9, 10. It also means 1.0, 1.1, 1.2. 1.3, ... , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described elsewhere in this disclosure.

The term "gel" in the sense of the present disclosure means that at least a part of the permeation layer comprises polymers that in water or organic solvent form a water or solvent-swollen network and/or a network of polymer chains that are water or solvent-soluble. Preferably the gel permeation layer comprises in swollen state >50% water and/or solvent, about >70% water and/or solvent, or about >90% water and/or solvent. When the gel is swollen only by water, it is often referred to as a hydrogel.

The term "elemental ions" refers to ions of elements such as, but not limited to the ions of hydrogen (i.e., a proton), an ion of a halogen, for example fluoride ion, chloride ion, bromide ion or iodide ion. Elemental ions can also be ions of any atom of the Periodic Table.

The term "functional group" refers to specific groups (moieties) of atoms or bonds within molecules (for example, organic chemical compounds and polymers) that are responsible for the characteristic chemical reactions of those molecules (or interactions with other molecules or ions). The same functional group can undergo the same or similar chemical reaction(s) regardless of the size of the molecule it is a part of.] However, its relative reactivity can be modified by other functional groups nearby. The atoms of functional groups are linked to each other and to the rest of the molecule by covalent bonds. Functional groups can also be charged, e.g. in carboxylate salts (—COO—), or ammonium salts which turns the molecule into a polyatomic ion or a complex ion. Functional groups binding to a central atom in a coordination complex are called ligands, but they can also interact with ions to form chemical gradients. The functional group can be tethered to a polymer, such as a group of atoms comprising, for example, carbon, nitrogen, oxygen that are covalently bonded together. The group of atoms may have additional substituents that also comprise, for example, carbon, nitrogen, oxygen, but can also include other atoms that are known in the field of organic chemistry, organometallic chemistry and polymer chemistry.

The term "nucleophile", as known to the skilled artisan in organic chemistry, refers to a chemical species that donates an electron pair to an electrophile to form a chemical bond in relation to a reaction. All molecules or ions with a free pair of electrons or at least one pi bond can act as nucleophiles. Because nucleophiles donate electrons, they are by definition Lewis bases. Nucleophilic describes the affinity of a nucleophile to the nuclei. Nucleophilicity, sometimes referred to as nucleophile strength, refers to a substance's nucleophilic character and is often used to compare the affinity of atoms. Neutral nucleophilic reactions with solvents such as alcohols and water are named solvolysis. Nucleophiles may take part in nucleophilic substitution, whereby a nucleophile becomes attracted to a full or partial positive charge.

Embodiments of the Invention

The present disclosure provides a polymer based gel and methods for selective and amplified detection of analytes of interest (e.g. sarin simulants) on the gel comprising at least one agent capable of fragmenting the analytes into two or more fragments, and comprising gradients of functional groups to concentrate the fragments for detection, remediation, separation or other purposes. In one such embodiment, the sarin simulant absorbs into a hydrogel, where it hydrolyzes upon contact with water producing $Cl^-$ (for sarin, the hydrolysis product would have been $F^-$). The $Cl^-$ is then concentrated via an ionic chemical potential gradient to a sensor, where it is detected. This technique has potential to amplify the capture efficiency of a sensor by a 1000-fold within a couple of minutes. For safety purposes, the concept is demonstrated using diethyl chlorophosphate, a simulant for sarin which hydrolyzes to yield $Cl^-$).

The directional transport of target ions up to several millimeters using hydrogel films containing built-in ionic chemical gradients is demonstrated herein. The gradient-imposed drift velocity was in the range of several micrometers per second, two-orders of magnitude higher than the directional transport of a molecular species. For the subset of important chemical agents, which hydrolyze yielding an ionic product, this approach provides an unprecedented opportunity for chemical sensing. The gradients used may also find application in the study of ion diffusion in biological systems, and could be used for surface-directed ion separation.

In one aspect, the present disclosure provides a polymer based gel for concentrating an analyte of interest, the gel comprising at least one agent capable of selectively and rapidly fragmenting an analyte of interest into two or more fragments, wherein at least one fragment is a target fragment indicative of the analyte of interest, and at least one spatial concentration gradient of functional groups having a gradient length, the functional groups capable of attracting or repelling the at least one target fragment towards at least one location in the gel, thereby concentrating the target fragment. In one embodiment, the gel further comprises at least one sensor located at the at least one location in the gel where the target fragment concentrates, the sensor capable of detecting the concentrated target fragment. The sensor can include, but is not limited to, a fluorescent dye, a colorimetric dye, or an electrochemical sensor. There are well-established electrochemical and fluorescent dye-based protocols for detecting $Cl^-$ and $F^-$. In one embodiment, the sensor is smaller than the gradient length.

When the gradient of functional groups works to attract the target fragment, the target fragment moves through or on the gel from a region containing a lower concentration of functional groups to a region containing higher concentration of functional groups. When the gradient of functional groups works to repel the target fragment, the fragment of interest moves through or on the gel from a region containing a higher concentration of functional groups to a region containing a lower concentration of functional groups.

The geometry of the gradient is not limiting, and can include any shape that allows for concentration of the target fragment to a particular location on a gel. For example, the gradient can have a radially symmetric geometry, a triangular geometry, where target fragments move toward one point of the triangle, or a linear gradient concentrating target fragments towards a center line or point, or other location or point within or on the gel.

In another embodiment, the at least one agent capable of fragmenting an analyte is a hydrolyzer or a nucleophile capable of fragmenting a phosphate-fluoride bond or a phosphate-chloride bond. The at least one agent capable of fragmenting an analyte can include, but is not limited to, oxime functional catalysts, metal chelate catalysts and enzymes. In one embodiment, the at least one agent capable of fragmenting the analyte is selected from 2-oxo-oximes, mono- and bis-quaternary pyridine oxo-oximes, Cu(II)-2,2'-bipyridyl, and alkaline phosphatase. In another embodiment, the pH of the gel can at a pH of 10 or higher, thereby capable of fragmenting a particular bond, for example, a phosphate-fluoride or a phosphate-chloride bond.

The target fragment can be ion, neutral molecule or charged molecule. In one embodiment, the target fragment can be ionic, and can include, but is not limited to, chloride ions, fluoride ions, and hydrogen ions.

The interactions between the target fragment and the functional groups can include, but not limited to, electrostatic, hydrogen bonding, and supramolecular interactions. In one embodiment, the gradient of functional groups is selected from a sulfate ion. In another embodiment, the gradient of functional groups is quaternary ammonium ion. The gradient can be a concentrating neutral-to-cationic gradient, or a neutral-to-anionic gradient. The gradient can be any composition capable of attracting or repelling ions, for example, $Cl^-$, $F^-$ and $H^+$. In one embodiment, the average distance between the edge of the gradient length to the region where the target fragment of the analyte of interest is concentrated is between about 10 μm and about 10 mm.

The gel may comprise additional agents capable of selectively and rapidly fragmenting different analytes into target fragments and additional functional group gradients to drive different target fragments to different locations within the same gel. Multiple analytes could be tested using the same gel.

The gel of the present disclosure can made of polymers including, but not limited to, poly(ethylene glycol) acrylate (PEGA)-based polymers, epoxide-based polymers, poly (ethylene glycol) (PEG)-based polymers, poly(vinylidene fluoride) (PVDF)-based polymers, polyacrylonitrile (PAN)-based polymers, polyacrylamide (PAA)-based polymers, polymethylmethacrylate (PMMA)-based polymers, polyvinyl chloride (PVC)-based polymers, and or mixtures thereof. In one embodiment, the gel comprises polyacrylamide.

The gel may be positioned on a substrate, including, but not limited to, glass, plastic, fabric, and combinations thereof. In another embodiment, the gel is a hydrogel and placed in a humid chamber, or be part of a device having a humid chamber to keep a sufficient amount of moisture in the hydrogel.

In another embodiment, the analyte of interest is a G type nerve agent. The analyte of interest can include, but is not limited to, sarin, soman, and cyclosarin.

In another aspect, a device comprising a gel as described herein is provided. The device can be attached to a data acquisition system, including, but not limited to, a computer, a hand-held device, a cell phone and a tablet. The device may also comprise a humid chamber for storage of the gel while the analyte is fragmented, and the target fragment concentrated and detected by the sensor(s). The device could turn the signals into the sensor into a visual representation of how much of the particular analyte or analytes is present and if present in a dangerous amount.

In another aspect, a method for the detection of an analyte is provided, the method comprising contacting a sample in or on the gel, fragmenting the analyte into two or more fragments, wherein at least one fragment is a target fragment, concentrating the target fragment through the gradient of functional groups to at least one location within the gel, and detecting the presence of the target fragment. The sample to be tested can be placed into or on the gel, or by exposure of the gel to air.

Some aspects of this disclosure provide a polymer-based gel for concentrating a fragment of an analyte of interest, the gel comprising: at least one agent capable of selectively and rapidly fragmenting an analyte of interest into two or more fragments, wherein at least one fragment is a target fragment indicative of the analyte of interest; and at least one spatial concentration gradient of functional groups having a gradient length, the functional groups capable of attracting or repelling the at least one target fragment towards at least one location in the gel, thereby concentrating the at least one target fragment. In other aspects, at least one sensor located at the at least one location in the gel, the sensor capable of detecting the concentrated target fragment of the analyte of interest. In additional aspects, at least one sensor is a fluorescent dye. In yet other aspects, at least one sensor is an electrochemical sensor. In additional aspects, at least one sensor is smaller than the gradient length.

This disclosure describes various embodiments of a polymer gel for detection of elemental ions comprising:
a) a polymer gel having a chemical potential gradient that can concentrate elemental ions by enthalpy driven transport; and
b) a plurality of functional groups, wherein the polymer gel is covalently bonded to the functional groups that provide the chemical potential gradient that transports the elemental ions to a region where the elemental ions are concentrated;
wherein an analyte in contact with the polymer gel is dissociated into molecular ions and elemental ions, and the elemental ions are transported by the chemical potential gradient of functional groups to the region where the elemental ions are concentrated (i.e., the focusing point of the chemical potential gradient).

In additional embodiments, the functional groups comprise a quaternary amine moiety, a sulfate moiety, a nitrate moiety, a tertiary amine moiety, a borate moiety, or a combination thereof. In other embodiments, the elemental ions are halide ions or hydrogen ions.

In various other embodiments, the polymer gel comprises a catalyst dispersed in the polymer gel. In some embodiments, the polymer gel comprises a layer of a catalyst or an enzyme on the surface of the polymer gel, or the catalyst or enzyme is imbedded at or near the surface of the polymer gel. In other embodiments throughout this disclosure, the catalyst comprises an enzyme. In yet other embodiments, the enzyme comprises diisopropyl fluorophosphatase (DFPase).

In yet other embodiments, the polymer gel comprises a polyacrylamide (PAAm) hydrogel, wherein the (PAAm) hydrogel is covalently bonded to the functional groups, and wherein the functional groups comprise a quaternary ammonium moiety, a sulfate moiety, a nitrate moiety, a tertiary amine moiety, a borate moiety, or a combination thereof. In additional embodiments, the hydrogel is planar and comprises at least about 80% water. Other embodiments of this disclosure comprise a nucleophile. In some embodiments of this disclosure, the nucleophile is not water or not hydroxide ion.

In yet other embodiments, the covalent bonds comprise amide bonds to (2-aminoethyl)trimethylammonium chloride (AETMA), sulfanilic acid, N,N-dimethylethylenediamine, 3-aminophenylboronic acid, or a combination thereof. In additional embodiments, the polymer gel comprises an electrode at the region where the elemental ions are concentrated. In some embodiments, an enthalpy driven rate of transport of elemental ions is at least about the same order of magnitude as an enthalpy driven rate of transport of molecular ions. In some additional embodiments, an enthalpy driven rate of transport of elemental ions is at least about one order of magnitude greater than an enthalpy driven rate of transport of molecular ions. In various other embodiments, an enthalpy driven rate of transport of elemental ions is at least two orders of magnitude greater than an enthalpy driven rate of transport for molecular ions. In other embodiments, the chemical potential gradient is linear, concentric (e.g. radially symmetric), or a combination thereof.

This disclosure provides various embodiments of an autonomic ion detector comprising:
a) a polymer gel having at least one chemical potential gradient that can concentrate elemental ions by enthalpy driven transport, wherein the elemental ions are halide ions, hydrogen ions, or a combination thereof;
b) a catalyst dispersed in the polymer gel to catalyze the dissociation of a sample into elemental ions and molecular ions;
c) a plurality functional groups comprising a quaternary amine moiety, a sulfate moiety, a nitrate moiety, a tertiary amine moiety, a borate moiety, or a combination thereof; wherein the polymer gel is covalently bonded to the functional groups that provide the chemical potential gradient that transports the elemental ions to a region where the ions are concentrated; and
d) an electrode to detect elemental ions at the region where the elemental ions are concentrated;
wherein a sample in contact with the autonomic ion detector is dissociated into molecular ions and elemental ions, and the elemental ions are transported by the chemical potential gradient of functional groups to the region where the elemental ions are concentrated and detected.

In other embodiments, the polymer gel comprises a polyacrylamide hydrogel, the hydrogel is planar, and the chemical potential gradient is linear, concentric, or a combination thereof.

This disclosure provides additional embodiments of a method of detecting elemental ions comprising:
a) contacting a sample with the ion detector of claim 12, wherein the sample comprises one analyte, or two or more different analytes that are hydrolyzed by the hydrogel into molecular ions and elemental ions, and the elemental ions are concentrated by the chemical potential gradient; and b) detecting the concentration of elemental ions.

In some embodiments of this disclosure the, the ion detector comprises an ion sensor for detecting the concentration of ions at the said region where the elemental ions are concentrated. In some embodiments the sensor comprises a working electrode, a reference electrode, a working electrode, or a combination thereof. In some embodiments the ion sensor comprises an ion selective membrane. In other embodiments, the membrane is selective for fluoride ion, chloride ion, bromide ion, or iodide ion. In other embodiments, the fluoride ion selective membrane comprises $EuF_2$-doped $LaF_3$ crystal, wherein the weight percent of the doped crystal is about 0.5% to about 10%, about 1% to about 5%, or about 3%.

This disclosure also provides embodiments of a method of detecting elemental ions comprising:
a) contacting a sample with a polymer gel having at least one chemical potential gradient that can concentrate elemental ions by enthalpy driven transport;
wherein the polymer gel is covalently bonded to a plurality of functional groups that provide the chemical potential gradient that transports the elemental ions to a region where the elemental ions are concentrated; and
b) detecting the concentration of elemental ions with an electrode at the region where the elemental ions are concentrated;
wherein the sample comprises one analyte, or two or more different analytes that are dissociated by contacting the polymer gel into molecular ions and elemental ions, and the elemental ions are transported by the chemical potential gradient of functional groups to the region where the elemental ions are concentrated and detected.

In various embodiments of the disclosed apparatus, methods of detection, and preparation of polymer gel gradients, the polymer gel comprises a catalyst or an enzyme dispersed in the polymer gel. In other embodiments the catalyst or enzyme is diisopropyl fluorophosphatase (DFPase). In yet other embodiments of this disclosure, the analyte is dissociated by hydrolysis.

In yet other embodiments, the polymer gel comprises a planar polyacrylamide (PAAm) hydrogel, wherein the planar (PAAm) hydrogel is covalently bonded to the functional groups, the functional groups comprise a quaternary amine moiety, a sulfate moiety, a nitrate moiety, a tertiary amine moiety, a borate moiety, or a combination thereof, and the chemical potential gradient is linear, concentric, or a combination thereof.

In additional embodiments, the elemental ions detected are hydrogen ions fluorine ions, chlorine ions, iodine ions, or a combination thereof. In other embodiments, the sample comprises G-type nerve agents, and the lower limit of detection (LOD) is about 1 ppb or less. In some embodiments the LOD is less than about 50 ppb, 5 ppb, 2 ppb, 0.5 ppb or less than about 0.1 ppb. In yet other embodiments, the hydrogel has a pH of about 9 to about 12, or a pH of about 9 to about 10. In other embodiments, detecting or determining the concentration of analytes can be performed in about 1 minute to about 60 minutes, about 1 minute to about 30 minutes, about 1 minute to about 15 minutes, about 1 minute to about 10 minutes, or about 1 minute to about 5 minutes. In additional embodiments, the enthalpy driven rate of transport of elemental ions is about $10^{-10}$ m/s to about $10^{-1}$ m/s, about $10^{-7}$ m/s to about $10^{-4}$ m/s, about $10^{-6}$ m/s to about $10^{-5}$ m/s, about $10^{-6}$ m/s to about $10^{-4}$ m/s, about $10^{-5}$ m/s to about $10^{-4}$ m/s, about $10^{-9}$ m/s, about $10^{-8}$ m/s, about $10^{-7}$ m/s, about $10^{-6}$ m/s, about $10^{-5}$ m/s, about $10^{-4}$ m/s, or about $10^{-3}$ m/s. In other embodiments, the polymer gel has 2, 3 or 4 chemical potential gradients.

In various aspects of the disclosure herein, the concentration gradient of functional groups attracts the fragment of interest, the target fragment moves through or on the gel from a region containing a lower concentration of functional groups to a region containing higher concentration of functional groups. In other aspects, the gradient of functional groups repels the fragment of interest, the target fragment moves through or on the gel from a region containing a higher concentration of functional groups to a region containing a lower concentration of functional groups. In additional aspects, the gel comprises additional gradients of functional groups capable of driving different target fragments to different locations within the same gel. In other aspects, the concentration gradient has a geometry that is radially symmetric. In yet other aspects, the gradient of functional groups to transport cations is selected from sulfate and nitrate.

In various aspects, the gradient of functional groups to transport anions is selected from quaternary ammonium and amine. In other aspects, the gradient of functional groups is a concentrating neutral-to-cationic gradient. In yet other aspects, the gradient of functional groups is a concentrating neutral-to-anionic gradient. In additional aspects, the target fragment is ionic. In yet other aspects, at least one agent capable of fragmenting an analyte is a hydrolyzer. In other aspects, at least one agent capable of fragmenting an analyte is a hydrolyzer capable of hydrolyzing a phosphate-fluoride or a phosphate-chloride bond.

In additional aspects, at least one agent capable of fragmenting an analyte is a nucleophile. In yet other aspects, at least one agent capable of fragmenting an analyte is a nucleophile capable of fragmenting a phosphate-fluoride or a phosphate-chloride bond. In other aspects, at least one agent capable of fragmenting an analyte is selected from oxime functional catalysts, metal chelate catalysts and enzymes. In additional aspects, the agent is selected from 2-oxo-oximes, mono- and bis-quaternary pyridine oxo-oximes, Cu(II)-2,2'-bipyridyl, and alkaline phosphatase. In other aspects, the target fragment is selected from a chloride ion, a fluoride ion, and a hydrogen ion. In other additional aspects, the analyte of interest is a G-type nerve agent. In yet other aspects the analyte of interest is selected from sarin, soman, cyclosarin, and diethyl chlorophosphate. In yet other aspects, the gel comprises polyacrylamide.

In various additional aspects, the gel of this disclosure further comprises a substrate to hold the gel. In other aspects, the substrate is selected from glass, plastic, fabrics and combinations thereof. In additional aspects, the gel is chemically treated to have a pH of about 10 or above, wherein the gel is capable of fragmenting a phosphate-chloride and a phosphate-fluoride bond. In other additional aspects, the gel has a thickness of about 100 nm to about 100 μm. In other aspects, the average distance between the edge of the gradient length to the region where the target fragment of the analyte of interest is to concentrated is between about 10 μm to about 10 mm.

In additional various embodiments of a polymer gel apparatus disclosed herein, or methods comprising the apparatus disclosed herein, the apparatus is connected to a data acquisition system. In other aspects, the data acquisition system is selected from a computer, a hand-held device, a cell phone and a tablet.

In various other aspects disclosed herein, a method of detection of an analyte having a phosphate-fluoride bond or phosphate-chloride bond comprises contacting a sample in or on the polymer, fragmenting the analyte into two or more fragments, wherein at least one fragment is a target fragment, concentrating the target fragment through the gradient of functional groups to at least one location within the gel, and detecting the presence of the target fragment. In other aspects, the analyte is selected from sarin, soman, and cyclosarin.

Figures 1A, 1D:
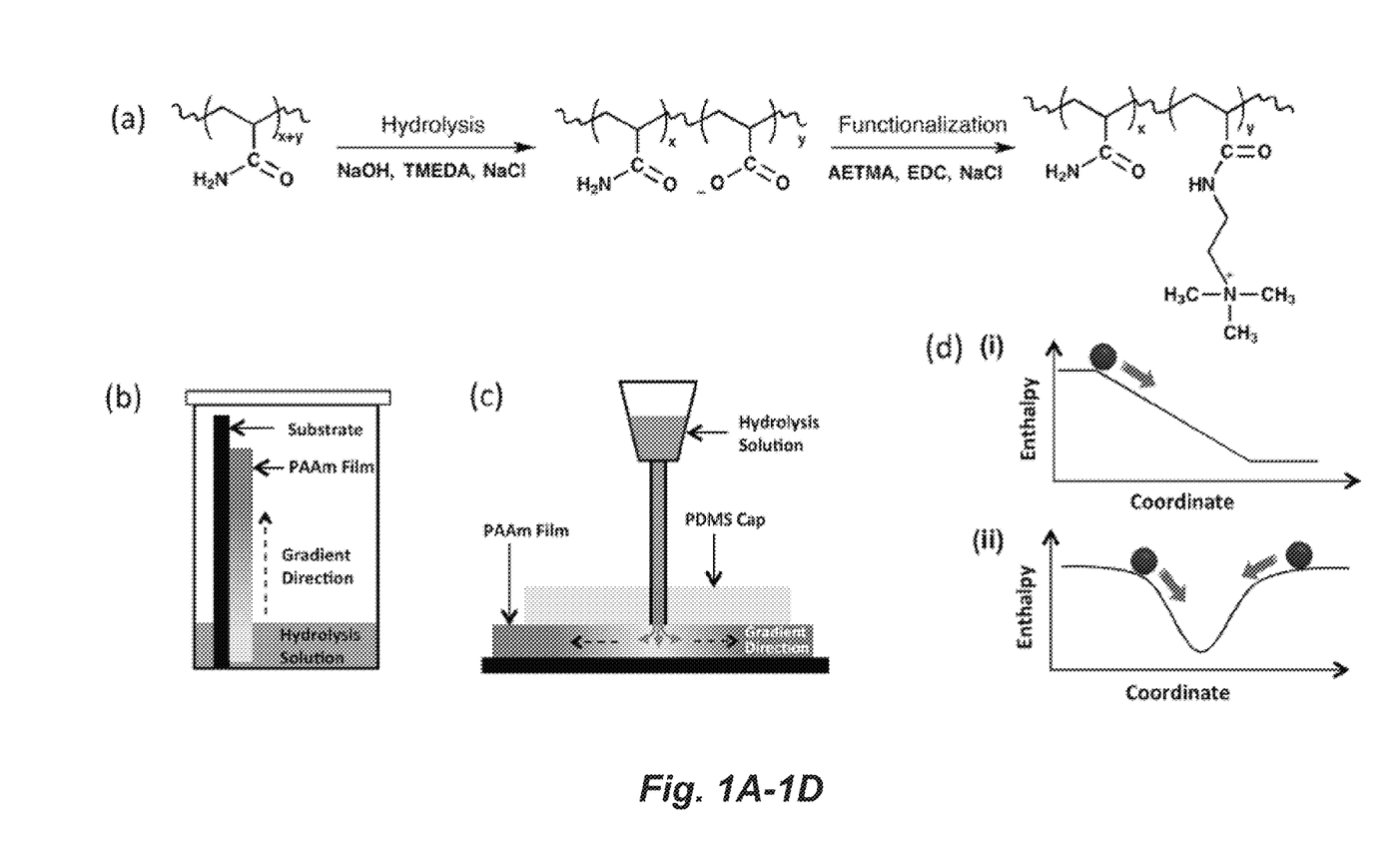
Figures 2A, 2F:
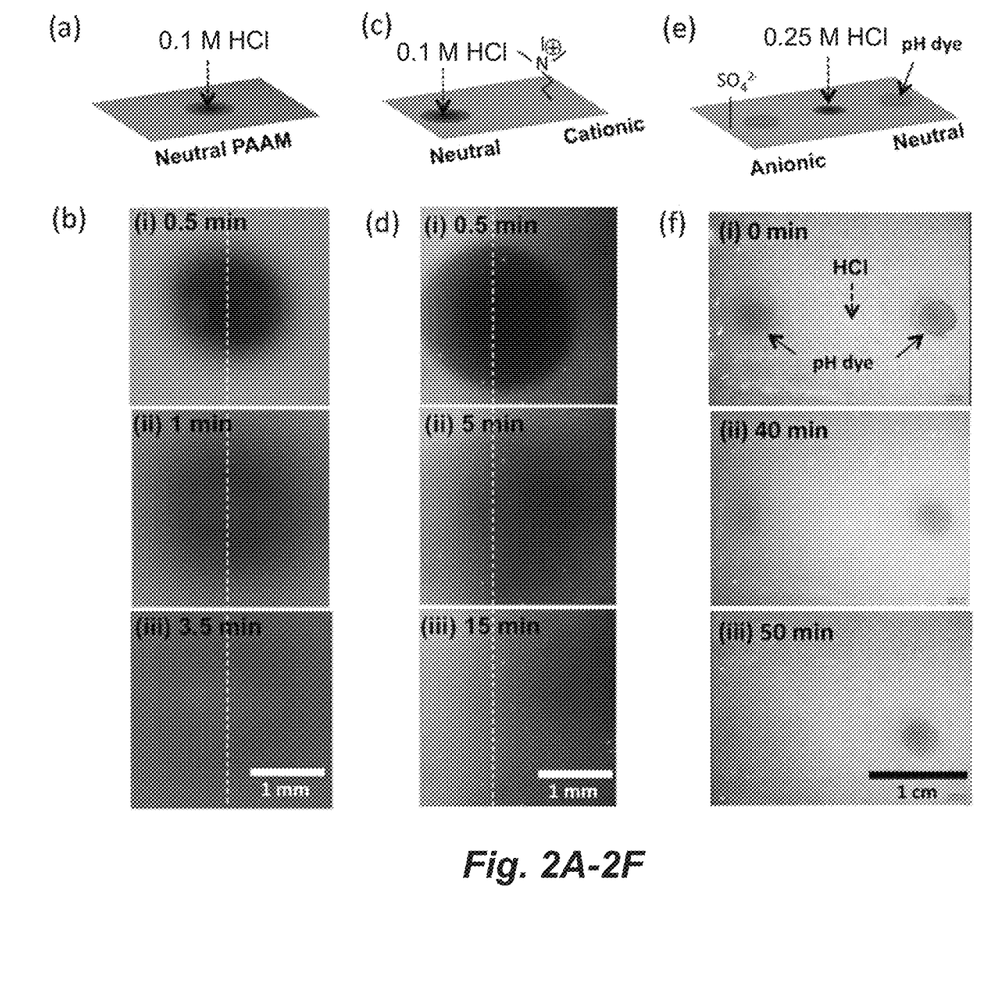

This disclosure provides a method of making a functional group gradient in a polyacrylamide (PAAm) hydrogel, the method comprising: making a hydrogel by mixing a solution that includes acrylamide, N,N'-methylenebisacrylamide and at least one initiator; exposing the solution to an energy source compatible with the initiator to polymerize the solution; and adding functional group gradients to the PAAm hydrogel by first forming a gradient in carboxylate density in the PAAm film through a spatialized variation in the hydrolysis of the amide groups on the PAAm followed by conjugating the carboxylates with amine-appended molecules containing desired functionalities. Other aspects further comprise repeating the above steps one or more times to interlace gradients containing different functional groups.

Additional embodiments disclosed herein provide a method of making a functional group gradient in a PAAm hydrogel which concentrates F ions, the method comprising: synthesizing the gel by mixing a solution that includes acrylamide, N,N'-methylenebisacrylamide and at least one initiator; exposing the solution to an energy source compatible with the initiator to polymerize the solution; and adding functional group gradients to the PAAm hydrogel by first forming a gradient in carboxylate density in the PAAm film through a spatialized variation in the hydrolysis of the amide groups on the PAAm followed by conjugating the carboxylates with (2-aminoethyl)trimethylammonium chloride.

Other additional embodiments disclosed herein provide a method of making a functional group gradient in a PAAm hydrogel which transports $H^+$ ions comprising, synthesizing the gel by mixing a solution that includes acrylamide, N,N'-methylenebisacrylamide and at least one initiator; exposing the solution to an energy source compatible with the initiator to polymerise the solution; and adding functional group gradients to the PAAm hydrogel by first forming a gradient in carboxylate density in the PAAm film through a spatialized variation in the hydrolysis of the amide groups on the PAAm followed by conjugating the carboxylates with (2-aminoethyl)trimethylammonium chloride followed by conjugating the carboxylates with sulfanilic acid.

Results and Discussion

Polyacrylamide Hydrogels with Chemical Tradients

Chemical gradients in the PAAm hydrogel were fabricated by first forming a gradient in carboxylate density in the PAAm film through a spatialized variation in the hydrolysis of the amide groups on the PAAm (FIG. 1A) following our reported method (Braun et al., *J Am. Chem. Soc.* 2015, 137, 5066), herein incorporated by reference. To create directional gradient, a dry PAAm film was dipped for 24 h in a chamber where the hydrolysis solution was filled up to ca. 2 mm from the bottom edge of the film (see FIG. 1B). The hydrolysis solution contained sodium hydroxide (6 mmol), N,N,N',N'-tetramethylethylenediamine (TMEDA) (18 mmol) and sodium chloride (3 mmol) in 20.0 g of Millipore water. As time passed, the hydrolysis solution diffused upward. Because the rate of the hydrolysis is slow at room temperature, this formed a gradient of carboxylate density across the PAAm film. The carboxylates were then transformed to the functionalities of interest (FIG. 1A) by conjugation with amine-appended molecules.

A cationic quaternary ammonium gradient was chosen to transport $Cl^-$, since the quaternary ammonium ion functionality reversibly binds $Cl^-$. The quaternary ammonium gradient was formed by immersing PAAm hydrogels containing carboxylate gradients for 24 h in a solution of N-(3-dimethylaminopropyl)-N'-ethylcarbodiimide hydrochloride (EDC) (0.78 mmol), (2-aminoethyl)trimethylammonium chloride hydrochloride (AETMA) (0.78 mmol), sodium chloride (3 mmol) in 20 g of Millipore water set to a pH of 4.5 by addition of few drops of diluted aqueous HCl. The geometry of gradient was controlled during the hydrolysis step as shown in FIG. 1B and FIG. 1C. The detailed gradient fabrication and characterization procedures were reported previously. Both a linear directional gradient with a length of ca. 7 mm and a radially symmetric gradient with a radius of ca. 4 mm were formed. In the final gradient, the affinity of $Cl^-$ for the quaternary ammonium ion creates an enthalpy gradient for $Cl^-$ as illustrated in FIG. 1D.

All experiments were performed with ca. 30 μm thick hydrogel films covalently attached to acrylate-functionalized glass substrates and carried out at 100% relative humidity (RH). Under these conditions, the hydrogel is ~90% water, and thus in the gradient-free region of the film, the ion diffusion coefficients are similar to in aqueous solutions. The thickness of the film is significantly less than the gradient length (several millimeters), and therefore, ion transportation is effectively two-dimensional.

Demonstration of Directional Transport of Ions

Before demonstrating the directional transport of $Cl^-$, it is important to ascertain the rate of $Cl^-$ diffusion in a gradient-free hydrogel. To remove residual $Cl^-$ remaining from the gradient fabrication, the film was dipped in 3 mM $NaNO_3$ for 2 h and then 5 mM NaOH for 2 h. To indicate the presence of $Cl^-$ in the hydrogel, 1 mM aqueous lucigenin, a fluorescent chloride indicator was sprayed (~75 μg/$cm^2$) on the surface of the films using an atomizer spray and $Cl^-$ (0.1 M HCl) was dosed using a tip. Lucigenin's fluorescence is quenched by $Cl^-$ with a Stern-Volmer constant of KSV=390 $M^{-1}$ but insensitive to $NO_3^-$. The presence of $Cl^-$ quenched the fluorescence of the lucigenin and the quenched spot was monitored continuously under a fluorescence microscopy as shown in FIG. 2B. It was seen that the quenched spot spread isotropically. A diffusion coefficient of $1\times10^{-9}$ $m^2/s$ was found using the Fick's $2^{nd}$ law. This value of the diffusion coefficient is comparable to the known value for $Cl^-$ in water.

The directional transport of $Cl^-$ using a neutral-to-cationic gradient consisting of neutral polymer (PAAm) at one end and the cationic quaternary ammonium functionalized PAAm on the other end was then investigated. FIG. 2D(i) shows the result when a tip coated with $Cl^-$ (0.1 M HCl) was contacted with the dye loaded hydrogel surface, leaving a trace of chloride ions, which quenched the fluorescence. It was seen that the quenched spot spreads anisotropically, with the overall transport being towards the quaternary ammonium-rich end of the gradient. The centroid of the quenched spot moved about 1 mm over 15 minutes (velocity $\sim1.1\times10^{-6}$ m/s), with the electrostatic interaction between the cationic quaternary ammonium group and the chloride ion being the primary driving force for the $Cl^-$ directional transport.

A similar experimental procedure was utilized to demonstrate cation transport, e.g., $H^+$, using PAAm hydrogel films containing an anionic sulfate gradient (sulfanilic acid was used as amine-appended molecule in the coupling reaction)

(FIG. 2F). Prior to analysis, the film was rinsed with DI water and pH of the film was ~7.4. The pH sensitive dye was sprayed on the film. One would expect to observe the movement of H$^+$ from changes in the dye color. However, no directional movement was seen, perhaps due to the strong binding of the dye to the H$^+$. To observe the directional movement, two drops (0.5 µL) of silica gels containing bromocresol blue dye (pH 6.0-7.6), a dye which is mostly used in applications that requires analysis near neutral pH (pH of 7) were placed in two different locations, one drop in the anionic area and other drop in the neutral area. The sol-gel prevented diffusion of the dye molecule into the hydrogel. The sol-gel-dye solution was prepared by hydrolysis of tetraethyl orthosilicate. Another advantage of the sol-gel was it enhanced the stability and durability of the dye in atmospheric condition. One drop of 0.2 µL of 0.25 M HCl was placed using a micro-syringe at a location centered between the two indicators as shown in FIG. 2F. A hint of color change (from blue to yellow) was seen after 40 min in the dye located in the anionic sulfate side. The color change progressed, and changed completely within 60 min. No change in color was observed in the dye region in the neutral area, suggesting that H$^+$ travelled under the influence of the gradient at approximately $2.7 \times 10^{-5}$ m/s.

Concentration of Target Fragment

Figure 3:
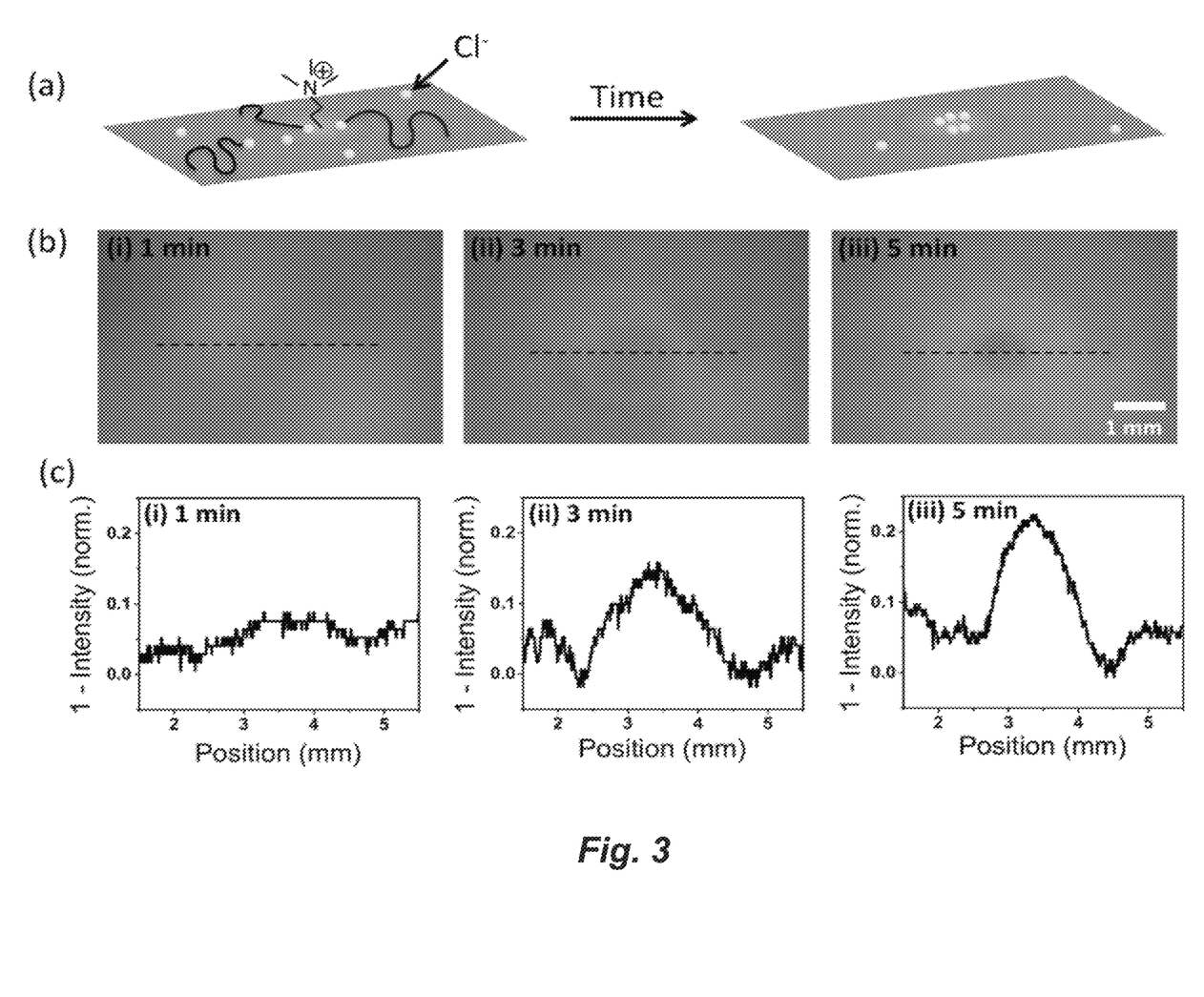

To evaluate the potential for concentration (an important property for many detection schemes), a radially symmetric neutral-to-cationic gradient was prepared. Lucigenin dye was introduced into the film using the same method discussed previously. ~30 µg/cm$^2$ of a 10 mM aqueous HCl solution (~11 ng/cm$^2$ of HCl) was sprayed onto the film surface using an atomizer and fluorescence images were taken overtime (FIG. 3B). A line profile of fluorescence over the radially symmetric gradient was plotted against position as a function of time. It was seen that the fluorescence intensity was nearly homogeneous shown in FIG. 3B(i), indicating that initially the atomizer-deposited Cl$^-$ has only diffused sufficiently to smear-out any spray droplet pattern. A short time later, as sufficient Cl$^-$ crossed the "event horizon", the outer edge of the gradient, and began to accumulate at the gradient center, florescence quenching in the gradient center begins. Over time, a distinct fluorescence quenching was observed at the center of the radially symmetric gradient indicative of an increase in Cl$^-$ concentration. Taking the Stern-Volmer constant as 390 M$^{-1}$ for lucigenin in aqueous solution, the concentration enhancement of Cl$^-$ in the concentrating region was found to be as high as 30-fold within 5 min. Interestingly, there is a bright ring around the edge of the gradient due to local depletion of Cl$^-$ in that region caused by the fact that Cl$^-$ is being pulled out of that region over the event horizon into the center of the gradient faster than it is being replenished by free diffusion into that region.

Concentration and Detection of G-type Nerve Agent Simulant

Figure 4:
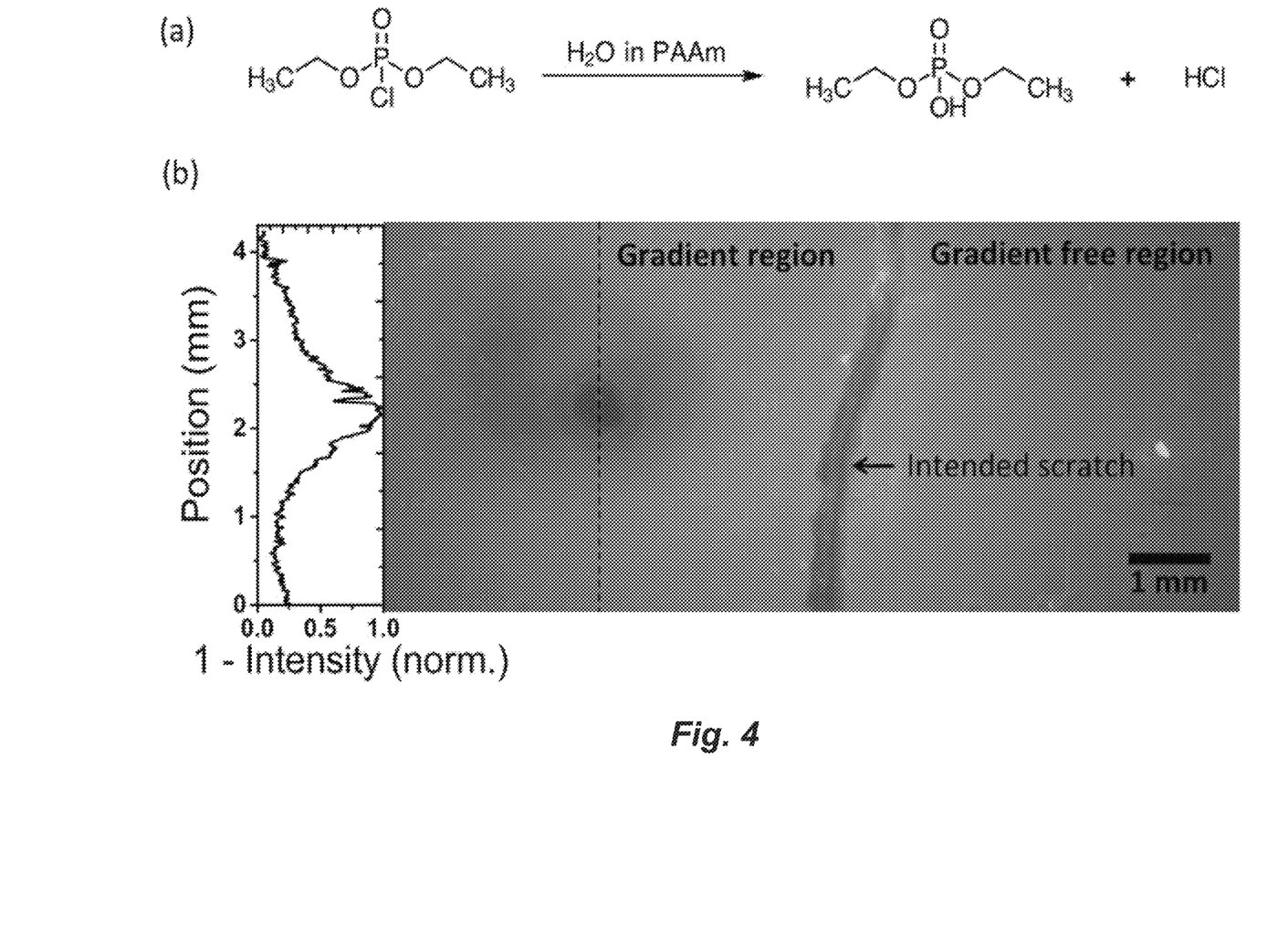

To demonstrate the potential for detection of sarin and other G-agents, ~15 µg/cm$^2$ of a 0.1 M solution of the sarin simulant, diethyl chlorophosphate, in ethyl acetate (~25 ng/cm$^2$ of the simulant) was sprayed on a PAAm hydrogel. As the diethyl chlorophosphate diffused into hydrogel, it hydrolyzed, yielding Cl$^-$. The rate of hydrolysis depends on the localized pH of the media. The pH of the hydrogel was measured to be ca. 10, which gives a half-life for sarin hydrolysis to be 5.4 minute. The hydrolysis rate could be accelerated by increasing the pH of the media or imbedding nucleophilic agents (such as oxime or catalyst) in the hydrogel. For one specific experiment, the hydrogel film on the substrate was physically separated into two regions by peeling a strip of hydrogel off the substrate, creating a physical barrier for ion exchange. One region contained a radially symmetric gradient and the other was gradient free. FIG. 4B shows a fluorescence image taken 30 minute after spraying the stimuli. A clear indication of Cl$^-$ concentration in the center of the radially symmetric gradient is the quenching of fluorescence at the center of the gradient.

Summary

The directional transport of target ions up to several millimeters using hydrogel films containing built-in ionic chemical gradients was demonstrated. The gradient-imposed drift velocity was in the range of several micrometers per second, two-orders of magnitude higher than the directional transport of a molecular species. For the subset of important chemical agents, which hydrolyze yielding an ionic product, this approach, could provide an unprecedented opportunity for chemical sensing. The gradients used may also find application in the study of ion diffusion in biological systems, and could be used for surface-directed ion separation.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Materials and Methods

Reagents 3-(trimethoxysilyl)propyl methacrylate (≥98%), trichloro (1H,1H,2H,2H-perfluorooctyl)silane (97%), acrylamide/N,N'-methylenebisacrylamide mixture (AAm/BisAAm mixture, 37:1 weight ratio), N,N,N',N'-tetramethylethylenediamine (99%), sodium hydroxide, sodium chloride, sodium nitrate, N-(3-dimethylaminopropyl)-N'-ethylcarbodiimide hydrochloride (EDC), sulfanilic acid sodium salt hydrate, (2-aminoethyl)trimethylammonium chloride hydrochloride (AETMA), bromothymol blue solution (dye content 95%), N,N'-dimethyl-9,9'-biacridinium dinitrate, and tetraethyl orthosilicate (TEOS), diethyl chlorophosphate, ethyl acetate purchased from Sigma Aldrich. 2,2-diethoxyacetophenone (DEAP, 98%) and dimethyl sulfoxide (DMSO) and Sylgard® 184 were purchased from Alfa Aesar.

Synthesis of PAAm Hydrogel Films 0.30 g of a 37:1 ratio mixture of AAm and BisAAm, was dissolved in 5.0 g Millipore water and the resulting monomer solution was shaken for 5 min using a Vortex mixer. After that, 0.10 g of DEAP dissolved in 1.0 g of DMSO was poured into the monomer solution and mixed for 15 min on the Vortex mixture. To remove dissolved oxygen/air from the polymerization solution, it was purged with nitrogen gas for 10 min. The solution filled into a cell and exposed to mercury UV lamp (Blak-Ray® longwave lamp B-100AP, 365 nm, 100 W, intensity: 21700 µW/cm2) for 2 h to polymerize it. The cell consisted of a trichloro(1H,1H,2H,2H-perfluorooctyl)silane monolayer coated top glass slide and a 3-(trimethoxysilyl)propyl methacrylate monolayer coated bottom glass slide. A 30-µm thick spacer was used in between them to control the thickness of the hydrogel. The resulting polyacrylamide (PAAm) hydrogel film was attached to the bottom slide which had been coated with the 3-(trimethoxysilyl)propyl methacrylate monolayer. All samples were washed with Millipore water to remove byproducts and unreacted species and dried in desiccator.

Dye-Silica Sols Preparation 3-4 drops of concentrated hydrochloric acid was added to 38 mL of water. This solution was poured into a solution of TEOS (30 mL) and ethanol (31 mL) with constant stirring using a magnetic bar. The solution was heated at 60° C. for 2 h and dried in a vacuum oven at 60° C. for 24 h. The molar ratio was calculated as TEOS:ethanol:water to be 1:4:16. To prepare dye-silica sols, 20 wt. % of the silica sol was dissolved in a 0.1% aqueous solution of bromothymol blue and stirring using a magnetic bar.

Example 2. Polymer Gel Comprising an Enzyme Catalyst for Trace Level Detection of an Analyte Highly toxic chemical warfare agents (CWAs) such as sarin and related compounds are highly toxic even at trace concentrations. Disclosed herein is a chemical force-based signal amplification method to detect airborne sarin as low as tier-1 ($6.90 \times 10^{-09}$ mg/cm$^3$ for 10 min) Acute Exposure Guideline Levels (AEGLs). As a proof of concept, detection of trace levels of an aerosol deposited sarin simulant, diisopropyl fluorophosphate (DFP) is demonstrated. The DFP is deposited on a hydrogel film and subsequently hydrolyzes upon contact with imbedded enzyme, diisopropyl fluorophosphatase (DFPase), producing P. The F$^-$ is then concentrated via a built-in ionic chemical gradient to a miniature electrochemical sensor. The net effect is a 30-fold amplification of the signal relative to a gradient-free system. This method is general for agents which hydrolyze into chemically detectable ionic species.

Figures 7A, 7C:
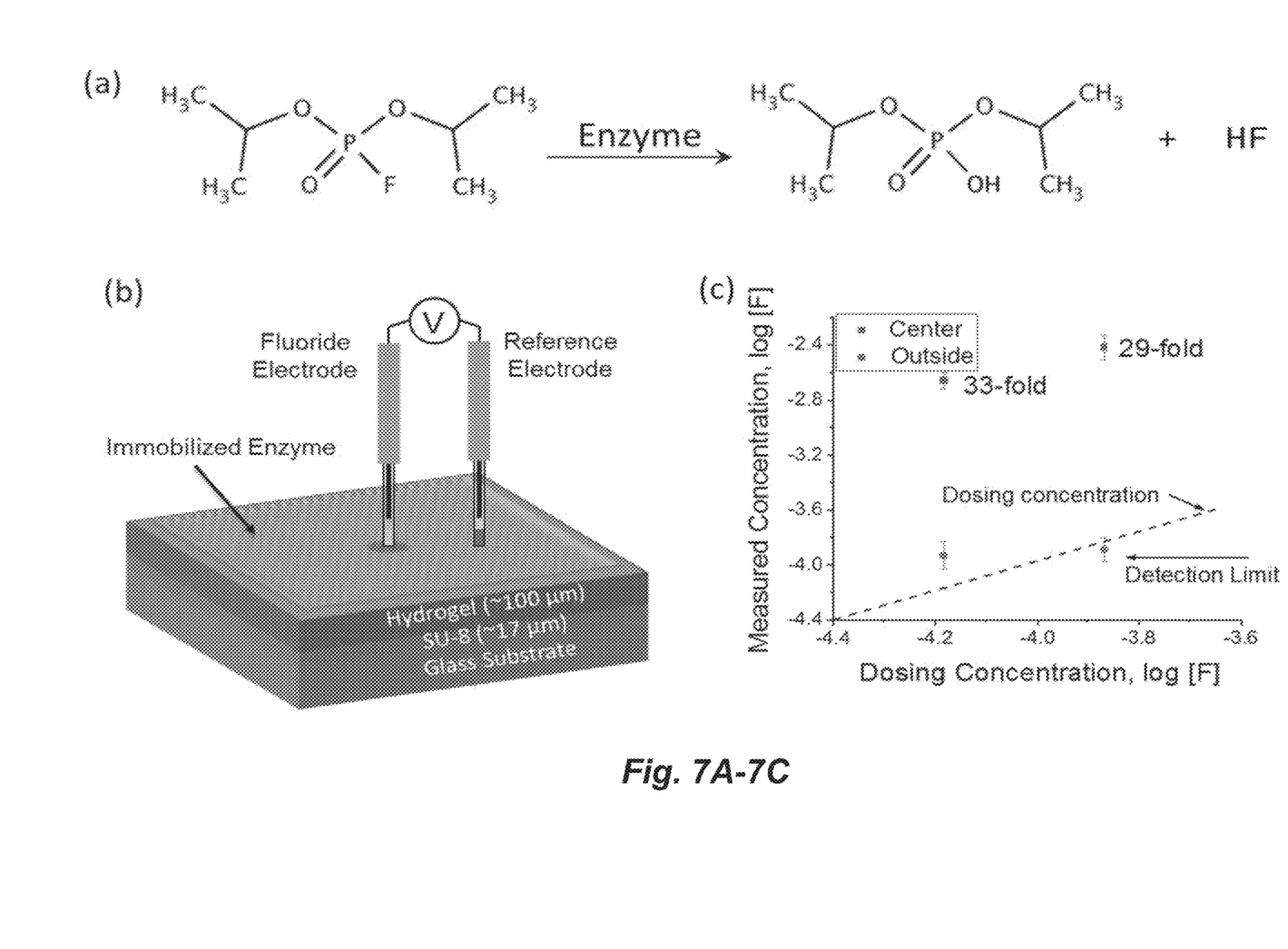

The agent first adsorbs into a catalyst containing gel film. Then, the catalyst hydrolyzes the agent, forming F$^-$ ions (FIG. 7a). The gel contains an internal ionic gradient that directionally transports the F– ions to a miniaturized F$^-$-ion-specific sensor imbedded in the gel at the focusing point of the chemical gradient (FIG. 7b). The advantages of this approach over concentration and detection of the initial agent are several fold. First, realization of a gradient which drives the transport of ions is much easier than realization of a gradient for uncharged molecular species. Second, ions generally diffuse quickly, and third, there are well-established, highly specific electrochemical sensors for ions.

Polyacrylamide (PAAm)-based hydrogels were chosen as the transport media since they can be easily functionalized and are relatively robust to a variety of chemical environments disclosed herein. For a proof-of-concept studies, simulants for highly toxic fluoride-containing "G series" chemical warfare agents were selected. The PAAm hydrogel contains ≥90% water and also offers ample space (mesh size ~12 nm) to accommodate the catalyst (enzyme) used to hydrolyze the P—F bonds in the simulant, yielding F$^-$ ions (for safety reasons, the concept is demonstrated using the sarin simulant DFP). The F$^-$ ions were detected electrochemically using a selective and quantitative approach that could detect Pions, one of the products of hydrolysis of sarin. Highly specific and sensitive electrochemical sensors for F$^-$ are commercially available, and can be adapted to be integrated with the disclosed hydrogels.

A 2 mm diameter electrochemical fluoride ion sensor was fabricated and placed at the center of the radially symmetric gradient in the gel. The gel system consisted of a thin layer (~5 µm) of the enzyme DFPase imbedded hydrogel on top of a thicker (ca. 100 µm) PAAm hydrogel containing radially symmetric neutral-to-cationic tertiary ammonium gradient, which is attached to a glass substrate using a 17 µm thick SU-8 layer. The SU-8 layer prevents any fluoride ion in the gel from reacting with the glass substrate. Proof-of-concept sarin detection studies were performed by spraying two different doses of a 5 mM solution of DFP in ethanol on the gel surface. After spraying the simulant, the gels were left in a chamber for 15 min at RH=100%. Due to the presence of DFPase, DFP is rapidly hydrolyzed foaming F$^-$ (at pH 7, DFP is hydrolyzed by DFPase at a rate of 78 µmol l$^{-1}$ s$^{-1}$). The F$^-$ are then driven to the center of the gradient by the imbedded radially symmetric neutral-to-cationic tertiary ammonium gradient. F$^-$ activities were monitored by the sensor at both the center of the gradient and outside of the gradient. FIG. 7c is a plot of dosing concentration (assuming all simulants were hydrolyzed to produce fluoride ion) versus measured concentration at these two regions. A 30-fold increase in F$^-$ concentration was measured at the center of the gradient relative to the dosing concentration (the theoretical upper bound was a 57-fold concentration enhancement).

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A polymer gel for detection of elemental ions comprising:
   a) a polymer gel having a chemical potential gradient that can concentrate elemental ions by enthalpy driven transport; and
   b) a plurality of functional groups, wherein the polymer gel is covalently bonded to the functional groups that provide the chemical potential gradient that transports the elemental ions to a region where the elemental ions are concentrated;
   wherein the polymer gel comprises a catalyst or an enzyme dispersed in the polymer gel, and the polymer gel is configured so that when an analyte is in contact with the polymer gel the analyte will dissociate into molecular ions and elemental ions, and the elemental ions will be transported by the chemical potential gradient formed by the functional groups to the region where the elemental ions are concentrated.

2. The polymer gel of claim 1 wherein the functional groups comprise a quaternary amine moiety, a sulfate moiety, a nitrate moiety, a tertiary amine moiety, a borate moiety, or a combination thereof.

3. The polymer gel of claim 2 wherein the elemental ions are halide ions or hydrogen ions.

4. The polymer gel of claim 1 wherein the polymer gel comprises a polyacrylamide (PAAm) hydrogel, wherein the (PAAm) hydrogel is covalently bonded to the functional groups, and wherein the functional groups comprise a quaternary ammonium moiety, a sulfate moiety, a nitrate moiety, a tertiary amine moiety, a borate moiety, or a combination thereof.

5. The polymer gel of claim 4 wherein the hydrogel is planar and comprises at least about 80% water.

6. The polymer gel of claim 4 wherein the covalent bonds comprise amide bonds to (2-aminoethyl)trimethylammonium chloride (AETMA), sulfanilic acid, N,N-dimethylethylenediamine, 3-aminophenylboronic acid, or a combination thereof.

7. The polymer gel of claim 6 wherein the chemical potential gradient is linear, concentric, or a combination thereof.

8. The polymer gel of claim 1 wherein the polymer gel comprises an electrode at the region where the elemental ions are concentrated.

9. An autonomic ion detector comprising:
a) a polymer gel having at least one chemical potential gradient that can concentrate elemental ions by enthalpy driven transport, wherein the elemental ions are halide ions, hydrogen ions, or a combination thereof;
b) a catalyst dispersed in the polymer gel to catalyze the dissociation of a sample into elemental ions and molecular ions;
c) a plurality functional groups comprising a quaternary amine moiety, a sulfate moiety, a nitrate moiety, a tertiary amine moiety, a borate moiety, or a combination thereof;
wherein the polymer gel is covalently bonded to the functional groups that provide the chemical potential gradient that transports the elemental ions to a region where the ions are concentrated; and
d) an electrode to detect elemental ions at the region where the elemental ions are concentrated;
wherein the polymer gel is configured so that when a sample is in contact with it the sample will dissociate into molecular ions and elemental ions, and the elemental ions will be transported by the chemical potential gradient formed by the functional groups to the region where the elemental ions are concentrated, where they are also detected.

10. The ion detector of claim 9 wherein the polymer gel comprises a polyacrylamide hydrogel, the hydrogel is planar, and the chemical potential gradient is linear, concentric, or a combination thereof.

11. A method of detecting elemental ions comprising:
a) contacting a sample with the ion detector of claim 10, wherein the sample comprises one analyte, or two or more different analytes that are hydrolyzed by the hydrogel into molecular ions and elemental ions, and the elemental ions are concentrated by the chemical potential gradient; and
b) detecting the concentration of elemental ions.

12. A method of detecting elemental ions comprising:
a) contacting a sample with a polymer gel having at least one chemical potential gradient that can concentrate elemental ions by enthalpy driven transport;
wherein the polymer gel is covalently bonded to a plurality of functional groups that provide the chemical potential gradient that transports the elemental ions to a region where the elemental ions are concentrated; and
b) detecting the concentration of elemental ions with an electrode at the region where the elemental ions are concentrated;
wherein the sample comprises one analyte, or two or more different analytes that are dissociated by contacting the polymer gel into molecular ions and elemental ions, and the elemental ions are transported by the chemical potential gradient formed by the functional groups to the region where the elemental ions are concentrated and detected.

13. The method of claim 12 wherein the polymer gel comprises a catalyst dispersed in the polymer gel.

14. The method of claim 13 wherein the catalyst comprises diisopropyl fluorophosphatase (DFPase).

15. The method of claim 12 wherein the polymer gel comprises a planar polyacrylamide (PAAm) hydrogel, wherein the planar (PAAm) hydrogel is covalently bonded to the functional groups, the functional groups comprise a quaternary amine moiety, a sulfate moiety, a nitrate moiety, a tertiary amine moiety, a borate moiety, or a combination thereof, and the chemical potential gradient is linear, concentric, or a combination thereof.

16. The method of claim 15 wherein the hydrogel has a pH of about 9 to about 12.

17. The method of claim 15 wherein the enthalpy driven rate of transport of elemental ions is about $10^{-6}$ m/s to about $10^{-5}$ m/s.

18. The method of claim 15 wherein the polymer gel has 2, 3 or 4 chemical potential gradients.

19. The method of claim 12 wherein the elemental ions detected are hydrogen ions, fluorine ions, chlorine ions, iodine ions, or a combination thereof.

20. The method of claim 12 wherein the sample comprises G-type nerve agents, and the lower limit of detection is about 1 ppb or less.

* * * * *